US010786287B2

(12) United States Patent
Beger et al.

(10) Patent No.: US 10,786,287 B2
(45) Date of Patent: Sep. 29, 2020

(54) MEDICAL INSTRUMENTATION AND METHOD

(71) Applicant: Aesculap AG, Tuttlingen (DE)

(72) Inventors: Jens Beger, Tuttlingen (DE); Josef Kozak, Tuttlingen (DE); Claudia Stoerk, Emmingen (DE)

(73) Assignee: Aesculap, Tuttlingen (DE)

( * ) Notice: Subject to any disclaimer, the term of this patent is extended or adjusted under 35 U.S.C. 154(b) by 112 days.

(21) Appl. No.: 15/679,395

(22) Filed: Aug. 17, 2017

(65) Prior Publication Data

US 2017/0340367 A1 Nov. 30, 2017

Related U.S. Application Data

(63) Continuation of application No. PCT/EP2016/051671, filed on Jan. 27, 2016.

(30) Foreign Application Priority Data

Feb. 26, 2015 (DE) ........................ 10 2015 102 776

(51) Int. Cl.
*A61B 17/70* (2006.01)
*A61B 34/20* (2016.01)
(Continued)

(52) U.S. Cl.
CPC ...... *A61B 17/7083* (2013.01); *A61B 17/7002* (2013.01); *A61B 17/84* (2013.01);
(Continued)

(58) Field of Classification Search
CPC . A61B 17/7002; A61B 17/7083; A61B 17/84; A61B 17/8863; A61B 34/20;
(Continued)

(56) References Cited

U.S. PATENT DOCUMENTS 6,036,691 A 3/2000 Richardson
6,226,548 B1 5/2001 Foley et al.
(Continued)

FOREIGN PATENT DOCUMENTS

DE 10045375 4/2002
DE 10314882 10/2004
(Continued)

OTHER PUBLICATIONS iPhone5; Apple Inc. Modified: Oct. 24, 2013; URL: <web.archive.org/web/20150312201031/https://support.apple.com/kb/SP655?locale=en_US> Accessed on Internet Archive, Sep. 15, 2019. (Year 2013).
(Continued)

*Primary Examiner* — Julianna N Harvey
*Assistant Examiner* — Christina Negrelli-Rodriguez
(74) *Attorney, Agent, or Firm* — Lipsitz & McAllister, LLC

(57) ABSTRACT

The invention relates to a medical instrumentation with a navigation system which comprises an optical detection unit comprising a camera, and a data processing unit coupled to the detection unit, with a stabilization element of a surgical fixation system and with a medical marking device which is held in a defined spatial arrangement on or is comprised by or formed by the stabilization element, the location and orientation of the marking device in space being determinable with the navigation system, it being possible for at least two images of the stabilization element and the marking device to be taken from a different orientation by means of the detection unit and for the shape of the stabilization element to be determined by the data processing unit on the basis of the two or more images. The invention also relates to a method for determining the shape of a surgical stabilization element.

19 Claims, 2 Drawing Sheets

(51) Int. Cl.
*A61B 17/88* (2006.01)
*A61B 17/84* (2006.01)
*A61B 90/00* (2016.01)
*A61B 34/10* (2016.01)

(52) U.S. Cl.
CPC .......... *A61B 17/8863* (2013.01); *A61B 34/20* (2016.02); *A61B 17/7032* (2013.01); *A61B 2034/108* (2016.02); *A61B 2034/2055* (2016.02); *A61B 2034/2057* (2016.02); *A61B 2090/037* (2016.02); *A61B 2090/3937* (2016.02); *A61B 2090/3983* (2016.02); *A61B 2090/3991* (2016.02)

(58) Field of Classification Search
CPC .... A61B 2034/2055; A61B 2034/2057; A61B 2034/2068
See application file for complete search history.

(56) References Cited

U.S. PATENT DOCUMENTS

| | | | |
|---|---|---|---|
| 7,561,733 | B2 | 7/2009 | Vilsmeier et al. |
| 7,763,030 | B2 | 7/2010 | Blau et al. |
| 7,809,184 | B2 | 10/2010 | Neubauer et al. |
| 7,835,778 | B2 | 11/2010 | Foley et al. |
| 7,862,568 | B2 | 1/2011 | Vilsmeier et al. |
| 7,922,731 | B2 | 4/2011 | Schumacher et al. |
| 7,957,831 | B2 | 6/2011 | Isaacs |
| 8,320,612 | B2 | 11/2012 | Knobel et al. |
| 8,534,848 | B2 | 9/2013 | Hauri et al. |
| 8,549,888 | B2 | 10/2013 | Isaacs |
| 9,314,281 | B2 | 4/2016 | Beger et al. |
| 9,585,700 | B2 | 3/2017 | Wehrle et al. |
| 2003/0078565 | A1 | 4/2003 | Vilsmeier et al. |
| 2005/0262911 | A1 | 12/2005 | Dankowicz et al. |
| 2007/0160439 | A1 | 7/2007 | Vilsmeier et al. |
| 2009/0249851 | A1* | 10/2009 | Isaacs ............... A61B 17/7011 72/31.04 |
| 2010/0100081 | A1 | 4/2010 | Tuma et al. |
| 2011/0270262 | A1 | 11/2011 | Justis et al. |
| 2011/0286098 | A1 | 11/2011 | Hauri et al. |
| 2013/0066387 | A1 | 3/2013 | Beger et al. |
| 2013/0268007 | A1 | 10/2013 | Rezach et al. |
| 2014/0005531 | A1 | 1/2014 | Taylor |
| 2014/0225999 | A1 | 8/2014 | Bracke et al. |
| 2014/0236159 | A1 | 8/2014 | Haider et al. |
| 2014/0311203 | A1 | 10/2014 | Crawford et al. |
| 2014/0316420 | A1* | 10/2014 | Ballard ............... A61B 17/7002 606/102 |
| 2015/0133945 | A1 | 5/2015 | Dushyant et al. |
| 2015/0182292 | A1 | 7/2015 | Hladio et al. |
| 2015/0305786 | A1 | 10/2015 | Wehrle et al. |
| 2016/0175013 | A1 | 6/2016 | Redmond |
| 2016/0242857 | A1 | 8/2016 | Scholl |
| 2017/0000568 | A1 | 1/2017 | O'Neil et al. |
| 2017/0340367 | A1 | 11/2017 | Beger et al. |
| 2018/0049809 | A1 | 2/2018 | Marti et al. |

FOREIGN PATENT DOCUMENTS

| | | |
|---|---|---|
| DE | 102004008870 | 10/2004 |
| DE | 102005026654 | 12/2006 |
| DE | 102008022254 | 11/2009 |
| DE | 102010016448 | 10/2011 |
| DE | 202015100313 | 3/2015 |
| DE | 102014102398 | 8/2015 |
| DE | 102015102776 | 9/2016 |
| EP | 1281365 | 2/2003 |
| EP | 1413257 | 2/2005 |
| EP | 1657678 | 5/2006 |
| EP | 1719472 | 11/2006 |
| EP | 1523950 | 2/2009 |
| EP | 2910206 | 8/2015 |
| WO | 0159708 | 8/2001 |
| WO | 03020146 | 3/2003 |
| WO | 2009135838 | 11/2009 |
| WO | 2011020505 | 2/2011 |
| WO | 2013164770 | 11/2013 |
| WO | 2014088801 | 6/2014 |
| WO | 2016134911 | 9/2016 |
| WO | 2017037113 | 3/2017 |

OTHER PUBLICATIONS

Apple App Store; My Tools: My AR Ruler & Light, iDaily Corp. URL: <https://apps.apple.com/hk/app/mytools-my-ar-ruler-light/id557839389?I=en>* earliest review for the app is dated Nov 17, 2012. Accessed Sep. 15, 2019 (Year: 2012).

Top 10 Apps Like Mytools—My AR Ruler & Light, URL: <https://appfelstrudel.com/a/557839389/alternative-to-mytools-my-ar-ruler-light.html> "First Release Sep. 28, 2012". Accessed Sep. 15, 2019. (Year 2012).

* cited by examiner

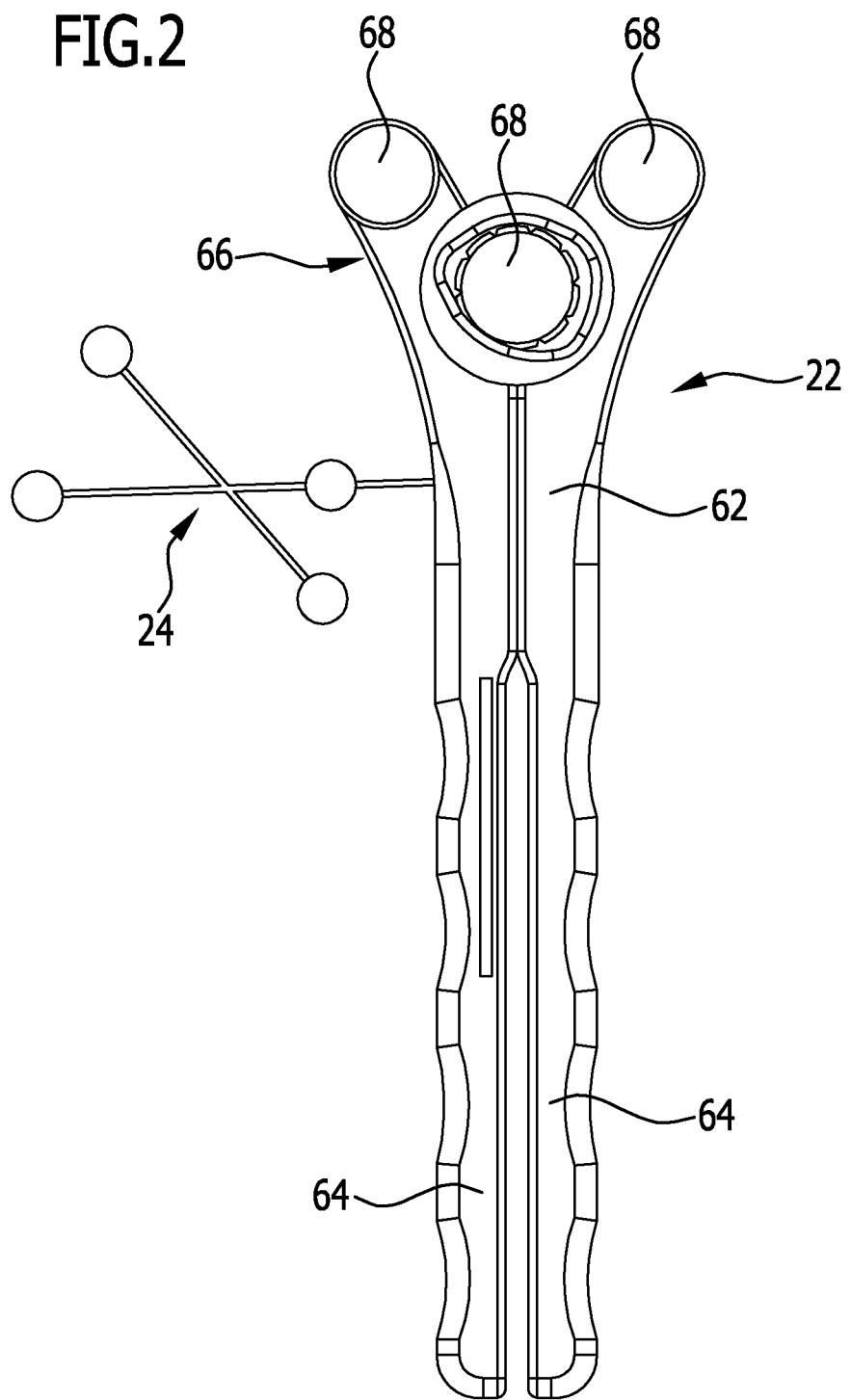

US 10,786,287 B2

MEDICAL INSTRUMENTATION AND METHOD

CROSS-REFERENCE TO RELATED APPLICATIONS

This application is a continuation patent application of international application number PCT/EP2016/051671, filed on Jan. 27, 2016, and claims the benefit of German application number DE 10 2015 102 776.3, filed Feb. 26, 2015, which are incorporated herein by reference in their entirety and for all purposes.

FIELD OF THE INVENTION

The present invention relates to a medical instrumentation.

The present invention also relates to a method for determining the shape of a surgical stabilization element.

BACKGROUND OF THE INVENTION

Surgical stabilization elements are used, in particular, as components of surgical fixation systems. For example, bones or bone fragments can be fixed relative to one another by means of such a fixation system. A typical field of application is spinal surgery during which vertebral bodies are to be secured so as to prevent movement relative to one another. Herein anchoring elements, for example, bone screws are anchored in the vertebral bodies and connected to one another by means of the stabilization element, for example, a rod.

Such a fixation system is described, for example, in DE 10 2010 016 448 A1.

To perform surgery with the least possible invasiveness, it is desirable to ascertain whether the stabilization element is suitable for connecting the anchoring elements to one another so as to achieve the desired fixation. If necessary, the shape of the stabilization element can be changed or a stabilization element can be selected from a plurality of available stabilization elements of different shape. The ascertainment, the change in shape and/or the selection preferably take place prior to implantation of the stabilization element.

Devices with which the shape of surgical stabilization elements can be changed are described in DE 103 14 882 A1, US 2005/0262911 A1 and U.S. Pat. No. 8,549,888 B2.

An object underlying the present invention is to provide an instrumentation and a method with which the shape of a surgical stabilization element can be determined in a simple way.

SUMMARY OF THE INVENTION

In a first aspect of the invention, a medical instrumentation with a navigation system is provided. The navigation system comprises an optical detection unit comprising a camera, and a data processing unit coupled to the detection unit. The instrumentation comprises a stabilization element of a surgical fixation system and a medical marking device which is held in a defined spatial arrangement on or is comprised by or formed by the stabilization element. The location and orientation of the marking device in space are determinable with the navigation system, it being possible for at least two images of the stabilization element and the marking device to be taken from a different orientation by means of the detection unit and for the shape of the stabilization element to be determined by the data processing unit on the basis of the two or more images.

In a second aspect of the invention, a method for determining the shape of a surgical stabilization element is provided, using an instrumentation in accordance with the first aspect. The location and orientation of the marking device in space are determinable with the navigation system, wherein at least two images of the stabilization element and the marking device are taken from a different orientation by means of the detection unit. The shape of the stabilization element is determined by the data processing unit on the basis of the two or more images.

BRIEF DESCRIPTION OF THE DRAWINGS

The foregoing summary and the following description may be better understood in conjunction with the drawing figures. There are shown in:

FIG. 2: a reshaping device of the instrumentation from FIG. 1.

DETAILED DESCRIPTION

Figure 1:
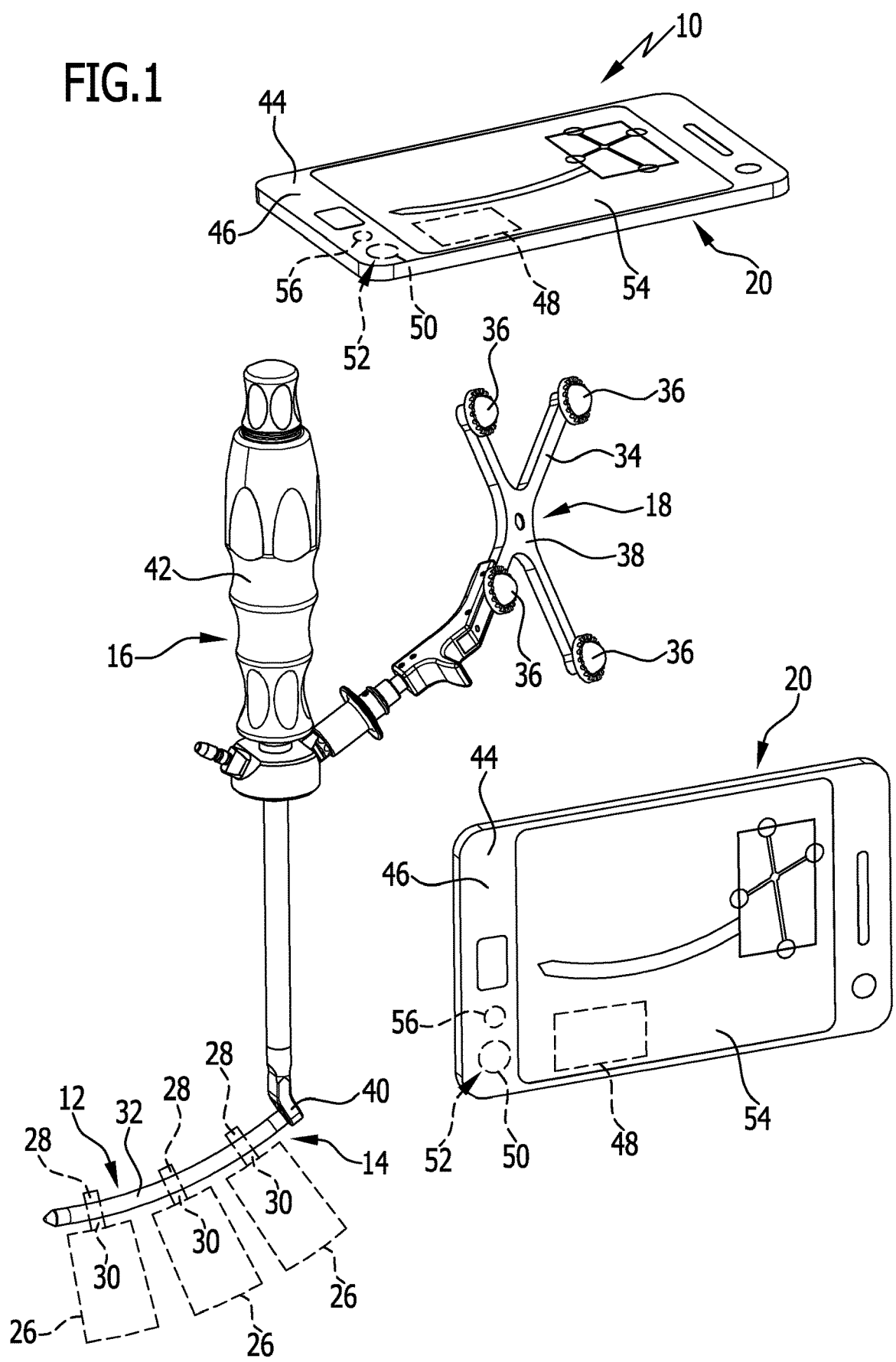
FIG. 1: a schematic perspective illustration of an instrumentation in accordance with the invention for performing an advantageous embodiment of the method in accordance with the invention.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrumentation with a navigation system which comprises an optical detection unit comprising a camera, and a data processing unit coupled to the detection unit, with a stabilization element of a surgical fixation system and with a medical marking device which is held in a defined spatial arrangement on or is comprised by or formed by the stabilization element, the location and orientation of the marking device in space being determinable with the navigation system, it being possible for at least two images of the stabilization element and the marking device to be taken from a different orientation by means of the detection unit and for the shape of the stabilization element to be determined by the data processing unit on the basis of the two or more images.

The present invention incorporates the concept that a medical marking device can be detected with respect to location and orientation and, accordingly, change in location and change in orientation by means of a medical navigation system. The navigation system comprises an optical detection unit with at least one camera with which images of the stabilization element including the marking device arranged thereon can be taken. At least two images are taken in succession from a different orientation, i.e., from a different relative position and direction of the navigation system and the stabilization element with the marking device. The marking device provides a reference and defines a reference coordinate system in which the shape of the stabilization element can be determined by the data processing unit on the basis of the images of the stabilization element. For this purpose, image processing algorithms can be stored for execution in the data processing unit, wherein the image processing algorithms analyze the images of the at least one camera and, using the location and/or orientation information on the basis of the marking device, determine the three-dimensional shape of the stabilization element with sufficient accuracy.

The instrumentation in accordance with the invention allows, in particular, determination of the shape of the stabilization element without the stabilization element having to be spatially fixed for this purpose. The expenditure in terms of equipment for determining the shape of the stabilization element can thereby be kept low. This also facilitates the handling of the instrumentation and reduces the effort for determining the shape.

The detection unit advantageously comprises precisely one camera in order to simplify the constructional design of the navigation system. The provision of a stereo camera is not necessary.

The stabilization element may be an implant which remains in the body or a trial implant used only temporarily, which may also be regarded as tool of the instrumentation.

As mentioned above, the stabilization element may, in particular, be a rod.

The stabilization element may be made of a plastic material or of a metal.

It is expedient for more than two images of the stabilization element and the marking device to be able to be taken in succession, on the basis of which the shape of the stabilization element is determinable, with the orientations and images differing from one another in pairs. The shape of the stabilization element can thereby be determined even more accurately.

If the stabilization element has a longitudinal extent, for example, in the configuration of a rod, the images are preferably taken with alignment of an optical axis of the at least one camera at an angle and, in particular, transversely to the longitudinal direction of the stabilization element. Between two images the camera is preferably rotated through 90° with respect to the longitudinal extent of the stabilization element.

For a constructionally simple design and a cost-effective manufacture of the instrumentation, it is expedient for the navigation system to be a hand-held, integrated navigation system. As used herein, "integrated" is, in particular, to be understood as meaning that the detection unit and the data processing unit are arranged in a common housing. A display unit of the navigation system is preferably arranged in the housing.

For example, the hand-held, integrated navigation system is a smartphone or a tablet computer. A data processing program with which data of the detection unit can be analyzed by the data processing unit and the shape of the stabilization element determined may be stored for execution on the smartphone or tablet computer.

It is advantageous for the navigation system to comprise a display unit which is coupled to the data processing unit and on which it is possible to show or provide the images of the stabilization element and/or instructions for a user for taking the images and/or a representation of the stabilization element, determined on the basis of the images.

It may be provided that the stabilization element comprises or forms marking elements of the marking device; for example, the marking elements are configured as preferably reflecting points or lines on the stabilization element.

The navigation system may comprise an illumination unit with which light, in particular, visible light can be emitted in the direction of the marking device. The illumination unit comprises, for example, at least one LED light source and is preferably comprised by the integrated, hand-held navigation system.

The marking device can be releasably fixed or fixable to the stabilization element directly or indirectly.

In an advantageous embodiment of the instrumentation, the marking device is integrally connected to the stabilization element, for example, is formed thereon or welded thereto.

A predetermined breaking point is expediently provided for separating the marking device from the stabilization element. After determination of the shape of the stabilization element, the marking device can be separated from it and the stabilization element implanted.

It is expedient for the instrumentation to comprise an implantation tool for the stabilization element, on which the stabilization element and the marking device are held. The implantation tool is, for example, hand-guided and allows the stabilization element to be preferably percutaneously and minimally invasively implanted. The marking device is arranged in a defined spatial arrangement in relation to the stabilization element by way of the implantation tool. The marking device may be releasably connectable to the implantation tool. This embodiment allows the shape of the stabilization element to be determined. At the same time, it is possible to track the stabilization element by way of the implantation tool with the marking device held thereon during the implantation. The handling of a surgical fixation system is thereby significantly simplified particularly during percutaneous implantation.

The instrumentation preferably comprises a reshaping device with which the shape of the stabilization element is changeable.

The reshaping device is, for example, a bending device for bending a rod, as which the stabilization element is configured.

It is expedient for an operator to be able to be provided by the data processing unit on an indication unit of the navigation system, for example, on a display unit, with shape changing information for handling the reshaping device, in order to convert the stabilization element from the determined shape into a prescribable shape. For example, the data processing unit can compare whether the determined shape of the stabilization element corresponds to a necessary, desired shape. The necessary shape can, for example, be determined by the relative positions of anchoring elements of the fixation system being detected with the proviso that the anchoring elements are to be connected to the stabilization element. If the shape determined on the basis of the images differs from the required shape, the stabilization element can be reshaped with the reshaping device. For this purpose, the operator can be provided with shape changing information on the display unit, and the handling of the instrumentation and the fixation system thereby considerably simplified.

In a corresponding manner, it is expedient for shape changing information to be transferable from the navigation system via a communication interface to the reshaping device, in order to convert the stabilization element from the determined shape into a prescribable shape. The reshaping device can give the stabilization element the prescribable, necessary shape, preferably without the intervention of the operator, on the basis of the shape changing information with which it is provided.

In particular, it is conceivable for the shape of the stabilization element to be detected in situ and/or preferably changed in situ by means of the reshaping device.

It is expedient for the instrumentation to comprise a further medical marking device which is held in a defined spatial arrangement on or is comprised by or formed by the reshaping device, for the location and orientation of the further marking device to be determinable with the navigation system, and for an operator to be able to be provided by the data processing unit on an indication unit of the navigation system, for example, on a display unit, with instructions for guiding the reshaping device. This makes it possible to track the reshaping device in space by means of the navigation system. The reshaping operation, for example, a bending plane or a bending radius can thereby be monitored.

As mentioned above, the present invention further also relates to a method. In accordance with the invention, a method for determining the shape of a surgical stabilization element uses an instrumentation of the aforementioned kind with a navigation system which comprises an optical detection unit comprising a camera, and a data processing unit coupled to the detection unit, with a stabilization element of a surgical fixation system and with a medical marking device which is held in a defined spatial arrangement on or is comprised by or formed by the stabilization element, the location and orientation of the marking device in space being determinable with the navigation system, wherein at least two images of the stabilization element and the marking device are taken from a different orientation by means of the detection unit and the shape of the stabilization element is determined by the data processing unit on the basis of the two or more images.

FIG. 1 shows a perspective illustration of an advantageous embodiment, denoted by reference numeral 10, of a medical instrumentation. The instrumentation 10 comprises a stabilization element 12 of a surgical fixation system and an implantation tool 16 for the stabilization element 12. The instrumentation 10 further comprises a medical marking device 18 and a medical navigation system 20. This is shown in two different orientations relative to the stabilization element 12 in FIG. 1, but present only once in the instrumentation 10.

The instrumentation 10 further comprises a reshaping device 22 shown in a side view in FIG. 2 for reshaping the stabilization element 12 and a further medical marking device 24 arranged thereon.

The fixation system 14 serves to fix vertebral bodies 26 shown schematically in FIG. 1 to prevent movement relative to one another. For this purpose, the fixation system 14 has anchoring elements 28 in the form of bone screws 30, which are fixed to the vertebral bodies 26. When the fixation system 14 is in use, the stabilization element 12, configured as rod 32, is fixed to the bone screws 30. The bone screws 30 are rigidly connected to one another by means of the rod 32.

To ensure the necessary relative position of the bone screws 30 and, therefore, of the vertebral bodies 26, it is important in practice for the rod 32 to have a desired, defined shape. The shape of the rod 32 is determined, as will be explained hereinbelow, by means of the navigation system 20.

In the present case, the medical marking device 18 is configured as so-called rigid body 34. The marking device 18 comprises a plurality of marking elements 36. The marking elements 36 are held on a common holder 38. The marking elements 36 are preferably of retroreflecting construction, in particular, for visible light.

In the instrumentation 10, the marking device 18 is held in a defined spatial arrangement indirectly on the rod 32. The implantation tool 16 serves this purpose. The rod 32 is, for example, held at a distal end 40 of the implantation tool 16 and assumes a defined spatial arrangement relative thereto. The marking device 18 is also held in a defined spatial arrangement on the implantation tool 16, for example, at or near a grip element 42 of the implantation tool 16.

For this reason, the spatial location and orientation of the rod 32 relative to the location and orientation of the marking device 18 is known. When the marking device 18 is tracked in space by means of the navigation system 20, the location and the orientation of the rod 32 can thereby also be concluded from this.

For easier handling and simple design of the instrumentation 10, the navigation system 20 is, in the present case, configured as hand-held, integrated navigation system. It is, for example, a smartphone or a tablet computer 44. As used herein, "integrated" is, in particular, to be understood as meaning that the components of the navigation system 20 are arranged in a common housing 46 of the navigation system 20. For example, the navigation system 20 has a data processing unit 48 arranged in the housing 46.

Furthermore, an optical detection unit 52 comprising a camera 50 is arranged in the housing 46. Precisely one digital camera 50 is expediently provided. Also arranged in the housing 46 is an indication unit, configured as display unit 54. In particular, the display unit 54 is a touch screen.

Furthermore, the navigation system 20 has an illumination unit 56 arranged in the housing 46 and, in particular, comprising an LED light source. With the illumination unit 56, light, in particular, visible light can be emitted in the direction of the marking device 18, and light reflected by its marking elements 36 can be received by the camera 50.

The data processing unit 48 comprises, for example, a microprocessor or is configured as such, on which an application program of the navigation system 20 can be executed. The application program includes, in particular, algorithms for the image processing.

With the instrumentation 10, the shape of the rod 32 can be easily determined using the navigation system 20. For this purpose, the operator can take a first image of the marking device 18 and the rod 32 with the camera 50. This corresponds, for example, to the arrangement of the navigation system 20 at the bottom in FIG. 1.

Subsequently, the operator can take a second image of the marking device 18 and the rod 32 in a changed orientation. This corresponds, for example, to the top illustration of the navigation system 20 in FIG. 1.

It is conceivable for the operator to take further images of the marking device 18 and the rod 32, with the images and the respective orientation differing from one another in pairs.

The data processing unit 48 is programmed to determine the shape of the rod 32 on the basis of the images taken in succession by the camera 50. This is possible, on the basis of the known spatial arrangement of the marking device 18 relative to the rod 32, owing to location and orientation of the rod 32 also being able to be concluded from location and orientation of the marking device 18 relative to the camera 50, as explained above.

It is found in practice that even with two images a sufficiently good determination of the shape of the rod 32 in three dimensions is possible by image processing.

Preferably, it can be indicated to the operator on the display unit 54 that and how, in particular, in which orientation, the images should be taken. It is expedient, in the case of a stabilization element 12 having a longitudinal extent, for an optical axis of the camera 50 to be aligned approximately transversely to the longitudinal extent of the stabilization element 12.

In FIG. 1 this is represented schematically by the navigation system 20 being rotated through approximately 90° in relation to the rod 32 in order to take the two images.

The images themselves or a representation of the stabilization element 12, determined on the basis of the images, can also be shown on the display unit 54. This is shown schematically in FIG. 1.

When the shape of the rod 32 is determined, the data processing unit 48 can ascertain whether the rod 32 has the necessary shape and, in particular, curvature, for the bone screws 30 to be able to be connected to one another as intended. If this is the case, the rod 32 can be implanted with the implantation tool 16.

It proves particularly advantageous that the marking device 18 is fixed to the implantation tool 16. By tracking the marking device 18, the rod 32 can be tracked during the implantation. On the display unit 54, the user can be given instructions for guiding the implantation tool 16. It is assumed that the position of the bone screws 30 is known in the reference coordinate system defined by the marking device 18. For example, one of the bone screws 30 is provided with a medical marking device, not shown in the drawings, and the position of the other bone screws 30 relative to this marking device is known. The rod 32 can thereby be tracked during insertion relative to the bone screws 30.

It is possible to determine the shape of the rod 32 preoperatively or also in situ.

FIG. 2 shows a reshaping device 22 for changing the shape of the rod 32. The reshaping device 22 is configured as bending device 62, in particular, as hand-held and hand-operated bending pliers. The bending device 62 comprises, for example, branches 64 pivotable relative to each other. Contact elements 68 for positioning on the rod 32 can be arranged at a distal end 66 of the branches. The rod 32 can be bent by manual actuation.

A further medical marking device 24 is preferably arranged on the bending device 62. As with the marking device 18, the marking device 24 can be tracked in space in a corresponding manner by the navigation system 20 and corresponds in its functioning thereto.

If the shape of the rod 32 that has been determined on the basis of the images does not correspond to the necessary shape, the rod 32 can be given the desired shape by bending with the bending device 62. For this purpose, it is, for example, possible for the data processing unit 48 to provide the operator with instructions on the display unit 54 as to how to actuate the bending device 62 for bending the rod 32.

The bending of the rod 32 can take place, in particular, in situ. In doing so, it is advantageous for the bending device 62 to be tracked by the navigation system 20 via the marking device 24. This makes it possible to give the operator instructions, in particular, in situ for bending the rod 32. Attachment points of the contact elements 68 on the rod 32, the bending plane and the bending radius can be checked and verified by tracking the bending device 62 relative to the rod 32. If necessary, the operator can be provided with instructions on the display unit 54 for repositioning the bending device 62 on the rod 32.

Instead of the hand-operated reshaping device 22, a mechanical reshaping device may also be used, as explained above. Via a communication interface, for example, wired or wireless, this reshaping device can be provided with shape changing information, in order for the reshaping device to give the rod 32 the desired shape.

LIST OF REFERENCE NUMERALS 10 instrumentation
12 stabilization element
14 fixation system
16 implantation tool
18 marking device
20 navigation system
22 reshaping device
24 marking device
26 vertebral bodies
28 anchoring element
30 bone screw
32 rod
34 rigid body
36 marking element
38 holder
40 distal end
42 grip element
44 smartphone
46 housing
48 data processing unit
50 camera
52 detection unit
54 display unit
56 illumination unit
62 bending device
64 branches
66 distal end
68 contact element

What is claimed is:

1. Medical instrumentation comprising:
a navigation system, the navigation system comprising an optical detection unit comprising a camera, and a data processing unit coupled to the detection unit,
a stabilization element of a surgical fixation system, the stabilization element having a shape, and
a medical marking device which is held in a defined spatial arrangement on or is comprised by or formed by the stabilization element,
a location and orientation of the marking device in space being determinable with the navigation system,
the detection unit being adapted to take a first image and at least one second image of the stabilization element and the marking device, with the first image and the at least one second image taken under different relative orientations of the camera and the stabilization element, and
the shape of the stabilization element being determined by the data processing unit using image processing algorithms to analyze the images on the basis of the first and the at least one second image.

2. Instrumentation in accordance with claim 1, wherein the stabilization element is a rod.

3. Instrumentation in accordance with claim 1, wherein more than two images of the stabilization element and the marking device are taken, on the basis of which the shape of the stabilization element is determinable, with the orientations and images differing from one another in pairs.

4. Instrumentation in accordance with claim 1, wherein the navigation system is a hand-held, integrated navigation system comprising a housing, the detection unit, the data processing unit and a display unit of the navigation system being arranged in the housing.

5. Instrumentation in accordance with claim 4, wherein the navigation system is a smartphone or a tablet computer.

6. Instrumentation in accordance with claim 1, wherein the navigation system further comprises a display unit which is coupled to the data processing unit, the display unit being adapted to show at least one of the following:
the images of the stabilization element,
instructions for an operator for taking the images, and
a representation of the stabilization element, determined on the basis of the images.

7. Instrumentation in accordance with claim 1, wherein the stabilization element comprises or forms marking elements of the marking device.

8. Instrumentation in accordance with claim 7, wherein the marking elements are configured as points or lines on the stabilization element.

9. Instrumentation in accordance with claim 1, wherein the marking device is releasably fixed or fixable to the stabilization element.

10. Instrumentation in accordance with claim 1, wherein the marking device is integrally connected to the stabilization element.

11. Instrumentation in accordance with claim 10, wherein a predetermined breaking point is provided for separating the marking device from the stabilization element.

12. Instrumentation in accordance with claim 1, further comprising an implantation tool for the stabilization element, on which the stabilization element and the marking device are held.

13. Instrumentation in accordance with claim 1, further comprising a reshaping device with which the shape of the stabilization element is changeable.

14. Instrumentation in accordance with claim 13, wherein:
the stabilization element comprises a rod, and
the reshaping device is a bending device for bending the rod.

15. Instrumentation in accordance with claim 13, wherein an operator is provided with shape changing information for handling the reshaping device by the data processing unit on an indication unit of the navigation system, in order to convert the stabilization element from the determined shape into a prescribable shape.

16. Instrumentation in accordance with claim 13, wherein shape changing information is transferable from the navigation system via a communication interface to the reshaping device, in order to convert the stabilization element from the determined shape into a prescribable shape.

17. Instrumentation in accordance with claim 13, further comprising a further medical marking device which is held in a defined spatial arrangement on or is comprised by or formed by the reshaping device,
wherein:
the location and orientation of the further marking device is determinable with the navigation system, and
an operator is provided with instructions for guiding the reshaping device by the data processing unit on an indication unit of the navigation system.

18. Instrumentation in accordance with claim 1, wherein the at least one second image comprises only one second image and the data processing unit determines the shape of the stabilization element on the basis of the first and the second image only.

19. Method for determining a shape of a surgical stabilization element, comprising:
using an instrumentation comprising:
a navigation system, the navigation system comprising an optical detection unit comprising a camera, and a data processing unit coupled to the detection unit,
a stabilization element of a surgical fixation system, the stabilization element having a shape, and
a medical marking device which is held in a defined spatial arrangement on or is comprised by or formed by the stabilization element,
determining a location and orientation of the marking device in space with the navigation system,
taking a first image of the stabilization element and the marking device by means of the detection unit,
modifying a relative orientation of the camera and the stabilization element from that of the first image and taking at least one second image of the stabilization element and the marking device from the modified relative orientation by means of the detection unit, and
determining, using image processing algorithms to analyze the images, the shape of the stabilization element by the data processing unit on the basis of the first and the at least one second image.

* * * * *

UNITED STATES PATENT AND TRADEMARK OFFICE
CERTIFICATE OF CORRECTION

PATENT NO. : 10,786,287 B2
APPLICATION NO. : 15/679395
DATED : September 29, 2020
INVENTOR(S) : Beger et al.

It is certified that error appears in the above-identified patent and that said Letters Patent is hereby corrected as shown below:

On the Title Page

"(73) Assignee: Aesculap, Tuttlingen (DE)" should read
-- (73) Assignee: Aesculap AG, Tuttlingen (DE) --

Signed and Sealed this
Fourteenth Day of February, 2023

Katherine Kelly Vidal
*Director of the United States Patent and Trademark Office*